United States Patent
Fujimori et al.

(10) Patent No.: US 8,177,712 B2
(45) Date of Patent: May 15, 2012

(54) BODY INSERTABLE APPARATUS AND BODY-INSERTABLE APPARATUS SYSTEM

(75) Inventors: Noriyuki Fujimori, Suwa (JP); Takemitsu Honda, Hiono (JP); Hiroshi Suzushima, Nagano (JP); Tatsuya Orihara, Hachioji (JP); Masatoshi Homan, Hino (JP); Kazutaka Nakatsuchi, Hino (JP)

(73) Assignee: Olympus Corporation, Tokyo (JP)

( * ) Notice: Subject to any disclaimer, the term of this patent is extended or adjusted under 35 U.S.C. 154(b) by 1420 days.

(21) Appl. No.: 11/631,351

(22) PCT Filed: Jun. 27, 2005

(86) PCT No.: PCT/JP2005/011764
§ 371 (c)(1),
(2), (4) Date: Feb. 26, 2007

(87) PCT Pub. No.: WO2006/006382
PCT Pub. Date: Jan. 19, 2006

(65) Prior Publication Data
US 2007/0232851 A1    Oct. 4, 2007

(30) Foreign Application Priority Data
Jul. 8, 2004   (JP) ................................. 2004-201932

(51) Int. Cl.
A61B 1/06 (2006.01)
A61B 1/00 (2006.01)
A61B 1/04 (2006.01)
(52) U.S. Cl. .......................... 600/176; 600/114; 600/102
(58) Field of Classification Search .................. 600/102, 600/109, 114, 127, 160, 176, 302
See application file for complete search history.

(56) References Cited

U.S. PATENT DOCUMENTS

| | | | |
|---|---|---|---|
| 5,604,531 A * | 2/1997 | Iddan et al. | 348/76 |
| 5,819,736 A | 10/1998 | Avny et al. | |
| 6,099,482 A * | 8/2000 | Brune et al. | 600/549 |
| 6,632,171 B2 * | 10/2003 | Iddan et al. | 600/106 |
| 6,709,387 B1 * | 3/2004 | Glukhovsky et al. | 600/109 |
| 7,448,993 B2 * | 11/2008 | Yokoi et al. | 600/114 |
| 7,511,733 B2 * | 3/2009 | Takizawa et al. | 348/68 |
| 7,647,090 B1 * | 1/2010 | Frisch et al. | 600/473 |

(Continued)

FOREIGN PATENT DOCUMENTS

JP    2001-137182    5/2001

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

To provide a capsule endoscope in which a degree of appearance of a sting-like member in a captured image is reduced, a capsule endoscope (2) includes an optical system (18) having a predetermined principal point, an imaging unit (19) which captures light focused by the optical system (18), and an attachment member (28) which is arranged at a predetermined position on a window portion (17a) having optical transparency and forming a portion of an outer casing member (17) housing the optical system (18) and the imaging unit (19). The capsule endoscope (2) further includes a traction member (29) having one end secured to the attachment member (28) and extending by a predetermined distance in a direction from the optical system (18) toward a position of the attachment member (28). Since the traction member (29) has such a structure, an appearance of an image of the traction member (29) can be reduced at the imaging unit (19).

22 Claims, 10 Drawing Sheets

U.S. PATENT DOCUMENTS

| | | | |
|---|---|---|---|
| 2002/0042562 A1* | 4/2002 | Meron et al. | 600/361 |
| 2002/0173718 A1 | 11/2002 | Frisch et al. | |
| 2003/0060734 A1* | 3/2003 | Yokoi et al. | 600/593 |
| 2003/0093088 A1* | 5/2003 | Long et al. | 606/129 |
| 2003/0120130 A1 | 6/2003 | Glukhovsky et al. | |
| 2003/0171653 A1* | 9/2003 | Yokoi et al. | 600/160 |
| 2003/0227547 A1* | 12/2003 | Iddan | 348/151 |
| 2004/0162469 A1* | 8/2004 | Imran | 600/310 |
| 2005/0143644 A1* | 6/2005 | Gilad et al. | 600/407 |
| 2005/0256372 A1* | 11/2005 | Yokoi et al. | 600/102 |
| 2006/0052667 A1* | 3/2006 | Palti et al. | 600/160 |
| 2007/0161885 A1* | 7/2007 | Kimchy | 600/407 |

FOREIGN PATENT DOCUMENTS

| | | |
|---|---|---|
| JP | 2003-019111 | 1/2003 |
| JP | 2003-210393 | 7/2003 |
| JP | 2005-103092 | 4/2005 |

* cited by examiner

BODY INSERTABLE APPARATUS AND BODY-INSERTABLE APPARATUS SYSTEM

TECHNICAL FIELD

The present invention relates to a body insertable apparatus which is introduced inside a subject and captures an image of an interior of the subject, and a body-insertable apparatus system including the body-insertable apparatus.

BACKGROUND ART

In recent years, a swallowable capsule endoscope has been proposed in a field of endoscope. The capsule endoscope has an imaging function and a radio communication function. After being swallowed by a subject from the mouth for an observation (examination), the capsule endoscope travels through inside body cavities, such as internal organs including a stomach and a small intestine following a peristaltic motion of the body cavities, and is eventually discharged naturally from the subject. The capsule endoscope has a function of capturing intra-subject images at 0.5-second intervals, for example, while traveling through the body cavities.

While traveling through the body cavities, the capsule endoscope externally and sequentially transmits image data obtained through the image capturing inside the body to an outside via radio communication, and the image data is accumulated in a memory provided outside. The subject carries a receiver having a radio communication function and a memory function, whereby the subject can move freely after swallowing the capsule endoscope until discharging the capsule endoscope. After the capsule endoscope is discharged, a doctor or a nurse can display images of internal organs based on the image data accumulated in the memory and make diagnosis (for example, see Patent Document 1).

Figure 9:
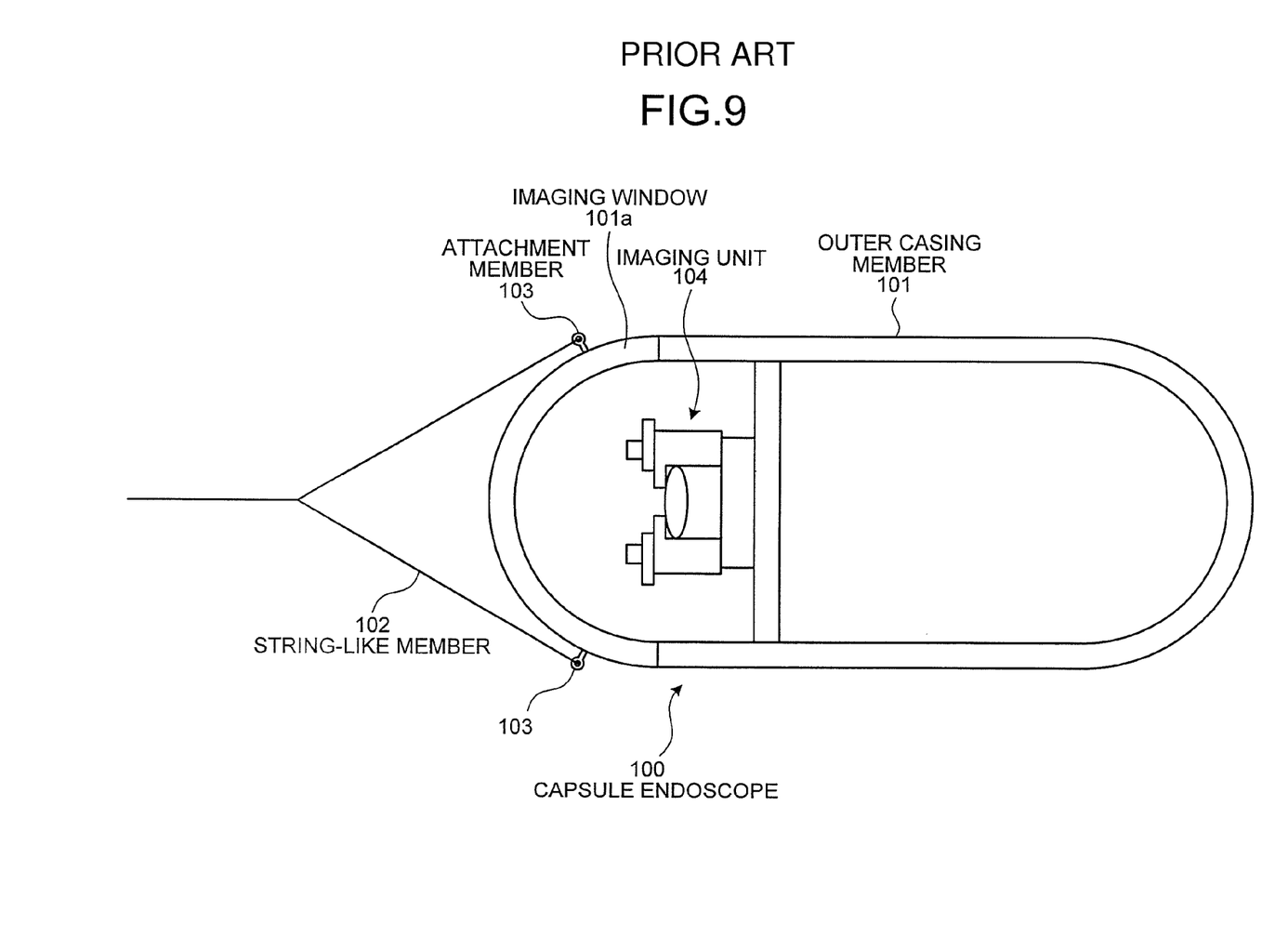
FIG. 9 is a schematic diagram of a structure of a conventional capsule endoscope.

Some propose a capsule endoscope including a string-like member attached to an outer casing portion for traction. FIG. 9 is a schematic diagram of a structure of such a capsule endoscope including a string-like member. Specifically, a capsule endoscope 100 shown in FIG. 9 includes an outer casing member 101 which defines an external shape of the capsule endoscope 100 and which is provided with an imaging window 101a corresponding to a field of view of an imaging unit 104, an attachment member 103 which is formed on the outer casing member 101, and a string-like member 102 having one end connected to the attachment member 103.

The string-like member 102 is employed to pull the capsule endoscope 100 inside the subject from outside. For example, when an operator wants to capture intra-subject images of an esophagus portion using a general capsule endoscope, a fast movement of the capsule endoscope makes it difficult to perform a sufficient imaging operation. When one end of the string-like member 102 is connected to the outer casing member 101 shown in FIG. 9, a doctor, for example, can pull another end of the string-like member 102 to adjust a moving speed and a position of the capsule endoscope 100 inside the subject. When the capsule endoscope has such a structure, it becomes possible to slow down the moving speed of the capsule endoscope for capturing plural intra-subject images even in an area such as an esophagus, and to capture the intra-subject images of an area where the capsule endoscope has already passed through.

Patent Document 1: Japanese Patent Application Laid-Open No. 2003-019111

DISCLOSURE OF INVENTION

Problem to be Solved by the Invention

When the capsule endoscope has the string-like member, however, the string-like member 102 may cause degradation of quality of the intra-subject images when placed within the field of view of the imaging unit 104. Such an inconvenience will be described below.

Figure 10:
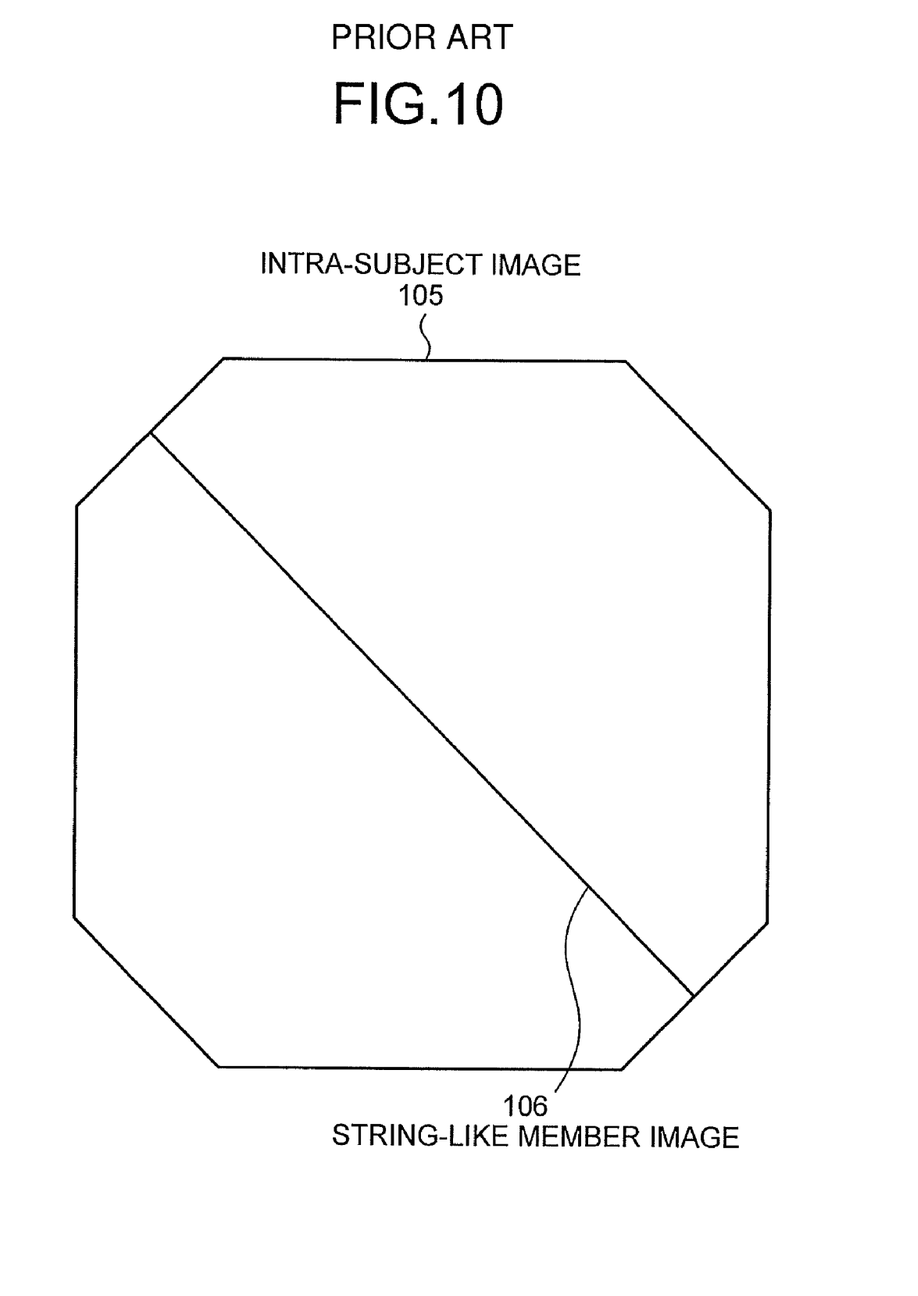
FIG. 10 is a schematic diagram of an intra-subject image captured by the conventional capsule endoscope.

In the capsule endoscope shown in FIG. 9, the imaging window 101a serves as a window portion through which external light is guided to the imaging unit 104 arranged inside. Therefore, if the string-like member 102 is present on an extension of the imaging window 101 relative to the imaging unit 104, the imaging unit 104 captures an intra-subject image including an image of the string-like member 102, whereby the quality of the intra-subject image is degraded. As shown in FIG. 10, for example, a string-like member image 106 may occupy a wide area of an intra-subject image 105 captured by the imaging unit 104. Then, the presence of such an image degrades the quality of the image, and may become an obstacle for the diagnosis and observation by the doctor or the like. Further, it cannot be denied that there is a possibility that the string-like member 102 which is present in the field of view of imaging reflects the light diffusely to cause flare and the flare appears in the intra-subject image. The flare in the image may become an obstacle for the diagnosis and the like by the doctor or the like.

To alleviate such inconveniences, the field of view of the imaging unit can be limited to a range where the string-like member 102 is not present so that the image of the string-like member 102 does not appear in the intra-subject image. When such a structure is employed, however, the field of view of the imaging unit is restricted by the string-like member 102. In the example of FIG. 9, for example, an image of an interior of the subject located opposite to the travel direction of the capsule endoscope 100 cannot be captured, and hence, such a structure is not preferable.

The present invention is made in view of the foregoing, and an object of the present invention is to provide a body-insertable apparatus such as a capsule endoscope which includes a string-like member for traction near a field of view of an imaging unit, wherein the string-like member appears in a captured image to a lessened degree, and a body-insertable apparatus system which includes the body-insertable apparatus as described above.

Means for Solving Problem

A body insertable apparatus according to one aspect of the present invention is introduced inside a subject and travels through the inside of the subject, and includes an optical system which focuses light introduced from outside onto a predetermined surface; an outer casing member which houses the optical system and includes a window portion to introduce light from the outside into the optical system; an attachment member which is formed at a predetermined portion of the window portion; and a traction member whose one end is secured by the attachment member and which extends by a predetermined distance in a direction from a principal point of the optical system toward the predetermined portion.

According to this body insertable apparatus, since the traction member is provided and the traction member extends by the predetermined distance in the direction from the principal point of the optical system toward the position of the attachment member. Therefore, an image of the traction member appears in an image focused on a predetermined plane by the optical system can be made small, whereby the degradation in the quality of the image obtained by the optical system can be suppressed.

In the body insertable apparatus, the attachment member may be formed on a portion on an extension of an optical axis of the optical system in the window portion, and the traction member may be arranged so that the traction member extends by the predetermined distance on the extension of the optical axis of the optical system.

Further, in the body insertable apparatus, the attachment member may be formed so that a longitudinal direction of the attachment unit coincides with the direction from the principal point of the optical system toward the predetermined portion.

Further, in the body insertable apparatus, the optical system may be arranged so that a direction of an optical axis coincides with a central axis in a longitudinal direction of the outer casing member.

Further, the body insertable apparatus may further include an imaging unit which generates image data based on light focused by the optical system; and a transmitting unit which transmits a radio signal containing the image data generated.

A body-insertable apparatus system according to another aspect of the present invention includes a body insertable apparatus which is introduced inside a subject, captures an intra-subject image, and transmits radio signals containing the intra-subject image captured; and a receiving device which receives the radio signals transmitted from the body insertable apparatus. The body insertable apparatus includes an optical system which focuses light introduced from outside onto a predetermined surface, an outer casing member which houses the optical system and includes a window portion to introduce light from outside to a field of view defined by the optical system, and a traction member whose one end is secured by an attachment member formed at a predetermined portion of the window portion and which extends by a predetermined distance in a direction from the principal point of the optical system toward the predetermined portion. The receiving device includes a receiving circuit which performs a predetermined receiving process on the radio signal received by a receiving antenna, and a signal processing unit which extracts image information from a signal subjected to the receiving process by the receiving circuit.

Effect of the Invention

The body-insertable apparatus and the body-insertable apparatus system according to the present invention, including the traction member which extends by the predetermined distance in the direction from the principal point of the optical system to the position of the attachment unit, is advantageous in that the image of the traction member in the image formed on the predetermined surface by the optical system can be reduced, and whereby the degradation of the quality of the image captured by the optical system can be suppressed.

EXPLANATIONS OF LETTERS OR NUMERALS

1 Subject
2 Capsule endoscope
3 Receiving device
4 Display device
5 Portable recording medium
6a to 6h Receiving antenna
9 Antenna selector
10 Receiving circuit
11 Signal processing unit
12 Control unit
13 Storage unit
14 A/D converter
15 Power supply unit
17 Outer casing member
17a, 17b Window portion
17c Cylindrical body
18, 21 Optical system
20, 22 Holder member
19, 23 Imaging unit
19a, 23a Imaging element
19b, 23b Imaging board
24, 25 Illuminating unit
24a, 25a Illuminating board
24b, 25b Illuminating element
26 Transmitting unit
26a Transmitting board
26b Transmitting antenna
27a, 27b Battery
28 Attachment member
29 Traction member
30 Principal point
31 Light receiving surface
32a Intra-subject image
32b Traction member image
33 Through hole
34 Retaining member
35, 36 Attachment unit/member
100 Capsule endoscope
101 Outer casing member
101a Imaging window
102 String-like member
103 Attachment unit
104 Imaging unit
105 Intra-subject image
106 String-like member image

BEST MODE(S) FOR CARRYING OUT THE INVENTION

Exemplary embodiments of a body insertable apparatus and a body-insertable apparatus system according to the present invention will be described below. It should be noted that the drawings are merely schematic and a relation between thickness and width of each portion, and a ratio of dimension of one portion to another may be different in an actual apparatus or system. Further, a dimensional relation and a ratio may be different from one drawing to another.

Figure 1:
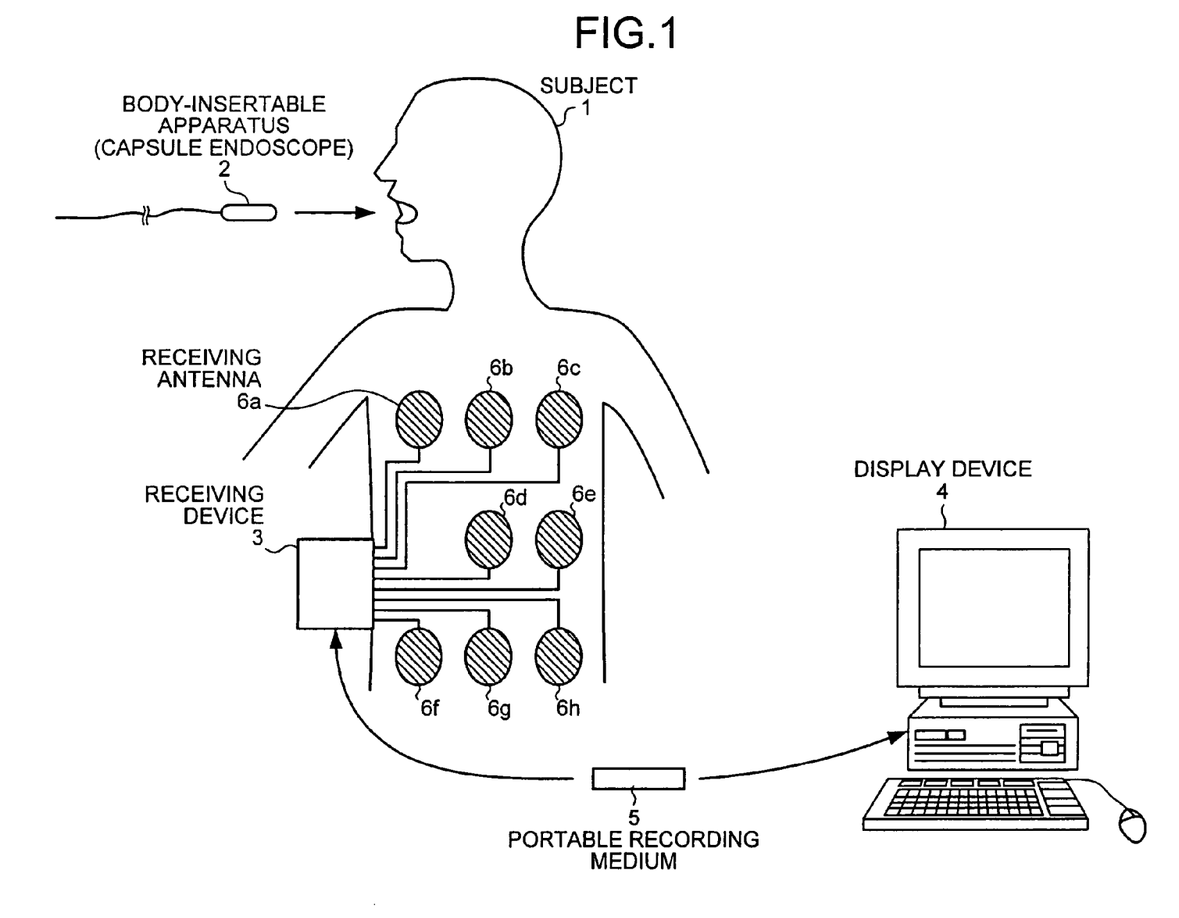
FIG. 1 is a schematic diagram of an overall structure of a body-insertable apparatus system according to an embodiment.

A body-insertable apparatus system according to an embodiment will be described. FIG. 1 is a schematic diagram of an overall structure of the body-insertable apparatus system according to the embodiment. As shown in FIG. 1, the body-insertable apparatus system according to the embodiment includes a capsule endoscope 2 which is introduced inside a subject 1 and travels through a predetermined path, a receiving device 3 which receives radio signals containing intra-subject information transmitted form the capsule endoscope 2, a display device 4 which displays a content of the intra-subject information contained in the radio signals received by the receiving device 3, and a portable recording medium 5 which serves to deliver information between the receiving device 3 and the display device 4.

The display device 4 serves to display an intra-subject image or the like captured by the capsule endoscope 2 based on the radio signals received by the receiving device 3. The display device 4 has a structure as a workstation or the like that display images based on data retrieved from the portable recording medium 5. Specifically, the display device 4 may directly display images as in a CRT display, and a liquid crystal display, or alternatively the display device 4 may output the image or the like onto other media as in a printer.

The portable recording medium 5 can be attached to and detached from each of the receiving apparatus 3 and the display device 4, and the portable recording medium 5 can record information or output information while attached to one of the receiving apparatus 3 and the display device 4. Specifically, while the capsule endoscope 2 travels through inside the body cavities, the portable recording medium 5 is attached to the receiving apparatus 3 and records the intra-subject images. On the other hand, when the capsule endoscope 2 is discharged from the subject 1, the portable recording medium 5 is removed from the receiving device 3 and attached to the display device 4, and the recorded data is read out by the display device 4. When the data transfer between the receiving device 3 and the display device 4 is performed with the portable recording medium 5 such as a Compact-Flash® memory, the subject 1 can move freely even while the capsule endoscope 2 is traveling through inside the subject 1, dissimilar to a case where the receiving device 3 and the display device 4 are connected by a cable.

Receiving antennas 6a to 6h are formed, for example, with a loop antenna. The loop antenna is arranged at a predetermined position on a body surface of the subject 2 during use, and preferably includes an attachment member for securing the loop antenna on the body surface of the subject 1.

Figure 2:
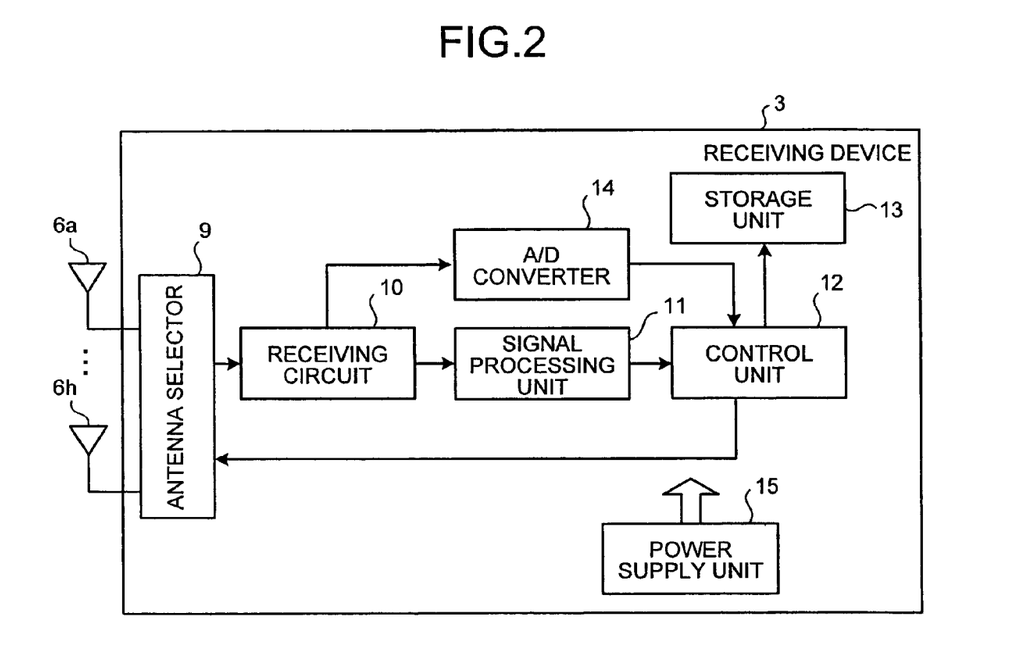
FIG. 2 is a block diagram of a structure of a receiving device provided in the body-insertable apparatus system.

The receiving device 3 serves to perform a receiving process of the radio signals received via one of the receiving antennas 6a to 6h. FIG. 2 is a block diagram of a structure of the receiving device 3. As shown in FIG. 2, the receiving device 3 includes an antenna selector 9 which selects an appropriate receiving antenna from the reception of the radio signals from the plural receiving antennas 6a to 6h, a receiving circuit 10 which performs processes such as demodulation on the radio signals received via the receiving antenna 6 selected by the antenna selector 9, and a signal processing unit 11 which serves to extract an intra-subject image or the like based on the processes radio signals. The receiving device 3 further includes a control unit 12 which controls an output of the extracted information, for example, in a predetermined manner, a storage unit 13 which stores the extracted information, an A/D converter which performs an A/D conversion of analog signals corresponding to strengths of the received radio signals, and a power supply unit 15 which supplies driving power to each element.

The antenna selector 9 serves to select an appropriate antenna for the reception of the radio signals from the plural receiving antennas 6a to 6h. Specifically, the antenna selector 9 has a function of selecting a predetermined receiving antenna 6 under the control of the control unit 12, and outputting the radio signals received via the selected receiving antenna 6 to the receiving circuit 10.

The receiving circuit 10 serves to perform predetermined processes such as demodulation on the radio signals received via the selected receiving antenna 6. The receiving circuit 10 has a function of outputting the analog signals corresponding to the strengths of the radio signals to the A/D converter 14.

The signal processing unit 11 serves to extract predetermined information from a signal which has been subjected to the predetermined processes by the receiving circuit 10. For example, if the receiving device 3 receives radio signals from an electronic device having an imaging function, the signal processing unit 11 extracts image data from the signals supplied from the receiving circuit 10.

The control unit 12 serves to perform an overall control including an antenna selecting operation at the antenna selector 9. Specifically, the control unit 12 has a function of transferring the information supplied from the signal processing unit 11 to the storage unit 13 and storing the information in the storage unit 13, while determining a receiving antenna 6 to be used based on digital signals (Received Signal Strength Indicator (RSSI), for example) that correspond to the received signal strength and that are supplied from the A/D converter 14 and giving instructions to the antenna selector 9.

The storage unit 13 serves to store the information extracted by the signal processing unit 11. As of a specific structure of the storage unit 13, the storage unit 13 itself may include a memory or the like and store the information therein. In the embodiment, however, the storage unit 13 has a function of writing the information into the portable recording medium 5 as described later.

The capsule endoscope 2 will be described. The capsule endoscope 2 of the embodiment is an example of the body-insertable apparatus as recited in the appended claims. Specifically, the capsule endoscope 2 includes a traction member so that the capsule endoscope 2 can be pulled from outside while inside the subject.

Figure 3:
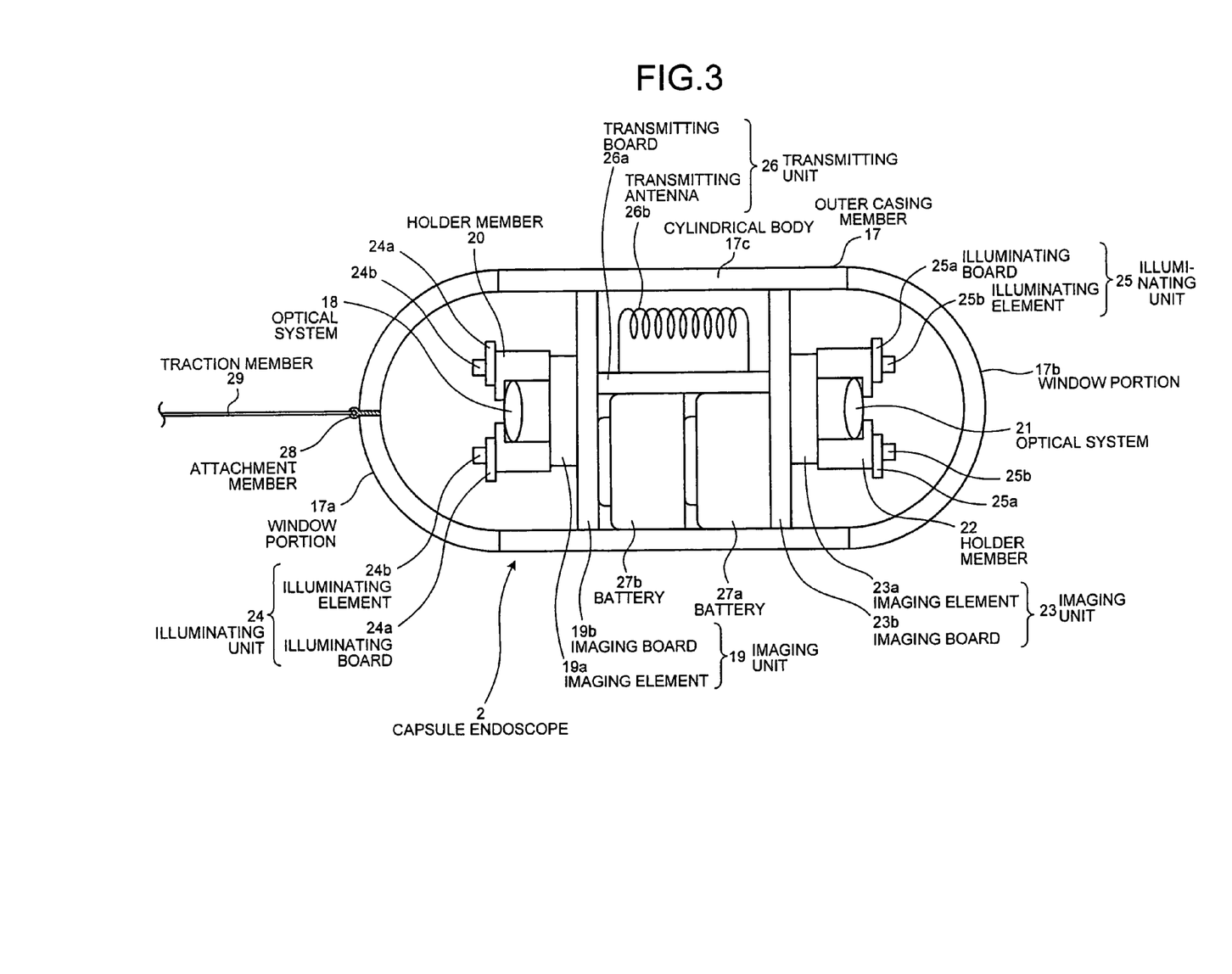
FIG. 3 is a schematic diagram of a structure of a capsule endoscope provided in the body-insertable apparatus system.

FIG. 3 is a schematic sectional view of a structure of the capsule endoscope 2. As shown in FIG. 3, the capsule endoscope 2 includes an outer casing member 17 which defines an external shape of the capsule endoscope 2 and houses elements described later, an optical system 18 which focuses light introduced from outside, a holder member 20 which holds the optical system 18, an imaging unit 19 which generates image data based on the light focused by the optical system 18, an optical system 21 which focuses light in a different range from the light focused by the optical system 18, a holder member 22 which holds the optical system 21, and an imaging unit 23 which generates image data based on the light focused by the optical system 21. Further, the capsule endoscope 2 includes an illuminating unit 24 which irradiates an external area corresponding to an intra-subject image captured by the optical system 18 and the imaging unit 19 with illuminating light, an illuminating unit 25 which irradiates an external area corresponding to an intra-subject image captured by the optical system 21 and the imaging unit 23 with illuminating light, a transmitting unit 26 which generates radio signals containing image data captured by the imaging units 19 and 23 with respect to an interior of the subject and transmits the same to the receiving device 3, and batteries 27a and 27b which supply driving power to element provided in the capsule endoscope 2. Further, the capsule endoscope 2 includes an attachment member 28 which is provided at a predetermined position on the outer casing member 17, and a traction member 29 which is connected to the outer casing member 17 by the attachment member 28.

The outer casing member 17 serves to define the external shape of the capsule endoscope 2 and to house the elements such as the optical system 18. In addition, windows 17a and 17b are formed in the outer casing member 17 to introduce the light from outside toward the optical systems 18 and 21, respectively. Specifically, the outer casing member 17 is formed with semi-spherical dome-shaped window portions 17a and 17b each arranged at one end in a longitudinal direction, and a cylindrical body 17c arranged between the window portions 17a and 17b and connected with the window portions 17a and 17b in a water-tight manner.

The optical systems 18 and 21 serve to focus external light coming through the window portions 17a and 17b, respectively, on a predetermined light receiving surface. In FIG. 3, the optical systems 18 and 21 are each formed with a single lens. The structure of the optical systems 18 and 21 is not limited thereto. As far as the optical systems 18 and 21 can focus the external light, the optical systems 18 and 21 may include plural lenses, or may be formed to have a different structure.

The imaging units 19 and 23 serve to generate image data of the intra-subject image based on the light focused by the optical systems 18 and 21, respectively. Specifically, the imaging units 19 and 23, respectively includes imaging elements 19a and 23a which convert the incoming light to electric signals, and imaging boards 19b and 23b on which a predetermined circuit is formed.

The imaging elements 19a and 23a include predetermined light receiving surfaces, respectively, and serve to generate electric signals corresponding to light intensity of light focused on the light receiving surface by the optical systems 18 and 21, respectively. Specifically, the imaging elements 19a and 23a are formed with a Charge Coupled Device (CCD), for example.

A circuit is formed on each of the imaging boards 19b and 23b to generate image data based on the electric signals supplied from the imaging elements 19a and 23a, respectively. The mage data generated by the circuit is supplied to the transmitting unit 26.

The illuminating unit 24 and 25 serve to output illuminating light to an area whose image is captured by the imaging units 19 and 23, respectively, in the subject. Specifically, the illuminating units 24 and 25 includes illuminating boards 24a and 25a and illuminating elements 24b and 25b, respectively. The illuminating elements 24b and 25b are formed with a Light Emitting Diode (LED), for example, and have a function of outputting the illuminating light under the control of a predetermined circuit formed on the illuminating boards 24a and 25a, respectively.

The transmitting unit 26 serves to generate radio signals containing image data obtained by the imaging units 19 and 23, and to transmit the radio signals to the receiving device 3. Specifically, the transmitting unit 26 includes a transmitting board 26a on which a circuit performing processes such as modulation is formed and which generates radio signals, and a transmitting antenna 26b which is employed to transmit the generated radio signals.

The attachment member 28 serves to fix the traction member 29 to the outer casing member 17. Specifically, the attachment member 28 is a rod-like body having a ring-like portion at one end, and arranged in such a manner that the rod-like body is buried in a hole formed in a predetermined area on the window portion 17a of the outer casing member 17, and the attachment member 28 has a function of securing the traction member 29 at the ring-like portion.

The traction member 29 serves to adjust the position and/or the travel speed of the capsule endoscope 2 from outside the subject after the capsule endoscope 2 is introduced into the subject. Specifically, the traction member 29 has one end secured to the outer casing member 17 via the attachment member 28 and another end formed with a string-like member which extends to the outside of the subject; the doctor or the like can control the travel speed or the like of the capsule endoscope 2 by holding the another end of the traction member 29. For example, when the capsule endoscope 2 is passing through the esophagus in the subject 1, the doctor or the like can exert a resistance to the capsule endoscope 2 in a direction opposite to the travel direction via the traction member 29, thereby slowing down the travel speed of the capsule endoscope 2 so that sufficient intra-subject images can be obtained.

A surface of each of the traction member 29 and the attachment member 28 is preferably treated to prevent reflection so that the surface does not appear in the intra-subject images. Preferably, the surface is painted in black or dark blue, for example. Further, since the traction member 29 is not used when the capsule endoscope 2 reaches the small intestine, for example, the traction member 29 may be formed from a biocompatible material or may be formed so as to be absorbed by the subject 1 over time.

Figure 4:
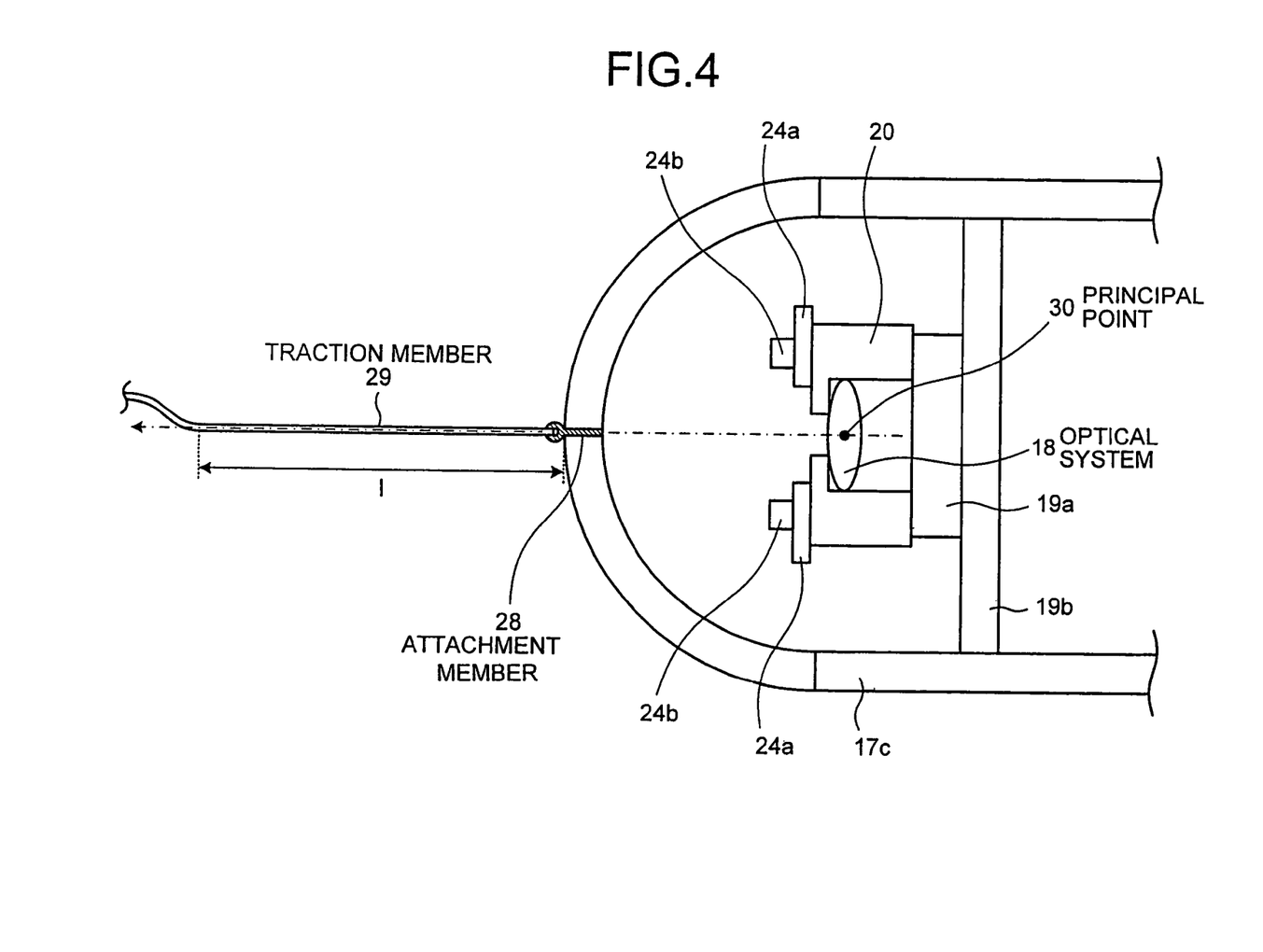
FIG. 4 is a schematic diagram of a detailed structure of a portion around a traction member in the capsule endoscope.

A positional relation among the attachment member 28, the traction member 29 whose one end is secured by the attachment member 28, and the optical system 18 in the capsule endoscope 2 will be described. FIG. 4 is a schematic diagram illustrating the positional relation.

As shown in FIG. 4, the traction member 29 is formed so that a direction of extension thereof coincides with a direction from a principal point 30 of the optical system 18 toward the attachment member 28 (direction of arrow shown by a chain line in FIG. 4) in a portion extending from the end secured by the attachment member 28 by a predetermined distance. In addition, the attachment member 28 is arranged on the outer casing member 17 so that the direction from the principal point 30 to the attachment member 28 coincides with a longitudinal direction of the attachment member 28.

In addition to the above-described features, in the embodiment, the attachment member 28 is arranged in a portion on an extension of an optical axis of the optical system 18 in the window portion 17a. As a result, the direction of extension of the traction member 29 coincides with the direction of the optical axis of the optical system 18. In addition, in the embodiment, the optical system 18 is arranged so that the direction of the optical axis coincides with the longitudinal direction of the outer casing member 17. Since the capsule endoscope 2 travels in the longitudinal direction of the outer casing member 17 within the subject 1, when the direction of the optical axis is positioned so as to coincide with the longitudinal direction of the outer casing member 17 of the capsule endoscope 2 of the embodiment, the direction of extension of the traction member 29 comes to coincide with the travel direction of the capsule endoscope 2.

Here, a predetermined distance l is set so that a sum of the distance between the optical system 18 and the attachment member 28 and the distance l is larger than an operating distance. In other words, the predetermined distance l is set so that an end of the extension of the traction member 29 in a predetermined direction is located farther than a focusing point of the optical system 18. Further, after the traction member 29 extends by the distance l as shown in FIG. 4, the traction member 29 may extend in any direction. Further, since the capsule endoscope 2 is configured to travel inside the subject 1, it is necessary to prevent the traction member 29 extending in a predetermined direction by the distance l from giving damages on a living tissue inside the subject 1. Therefore, the traction member 29 is formed with an elastic member or a flexible member so that at least a portion corresponding to the predetermined distance l maintains an extended state in the predetermined direction while no external force is applied though the portion is easily deformed when an external force is applied, for example, when the portion is brought into contact with the living tissue in the subject 1.

Advantages of the capsule endoscope 2 provided in the body-insertable apparatus system of the embodiment will be described. In the embodiment, the capsule endoscope 2 has a structure in which the traction member 29 extends by the predetermined distance l in a direction coinciding with the direction from the principal point of the optical system 18 toward the attachment member 28, whereby the image of the traction member 29 appears in the intra-subject image captured by the imaging unit 19 to a reduced degree.

Figure 5:
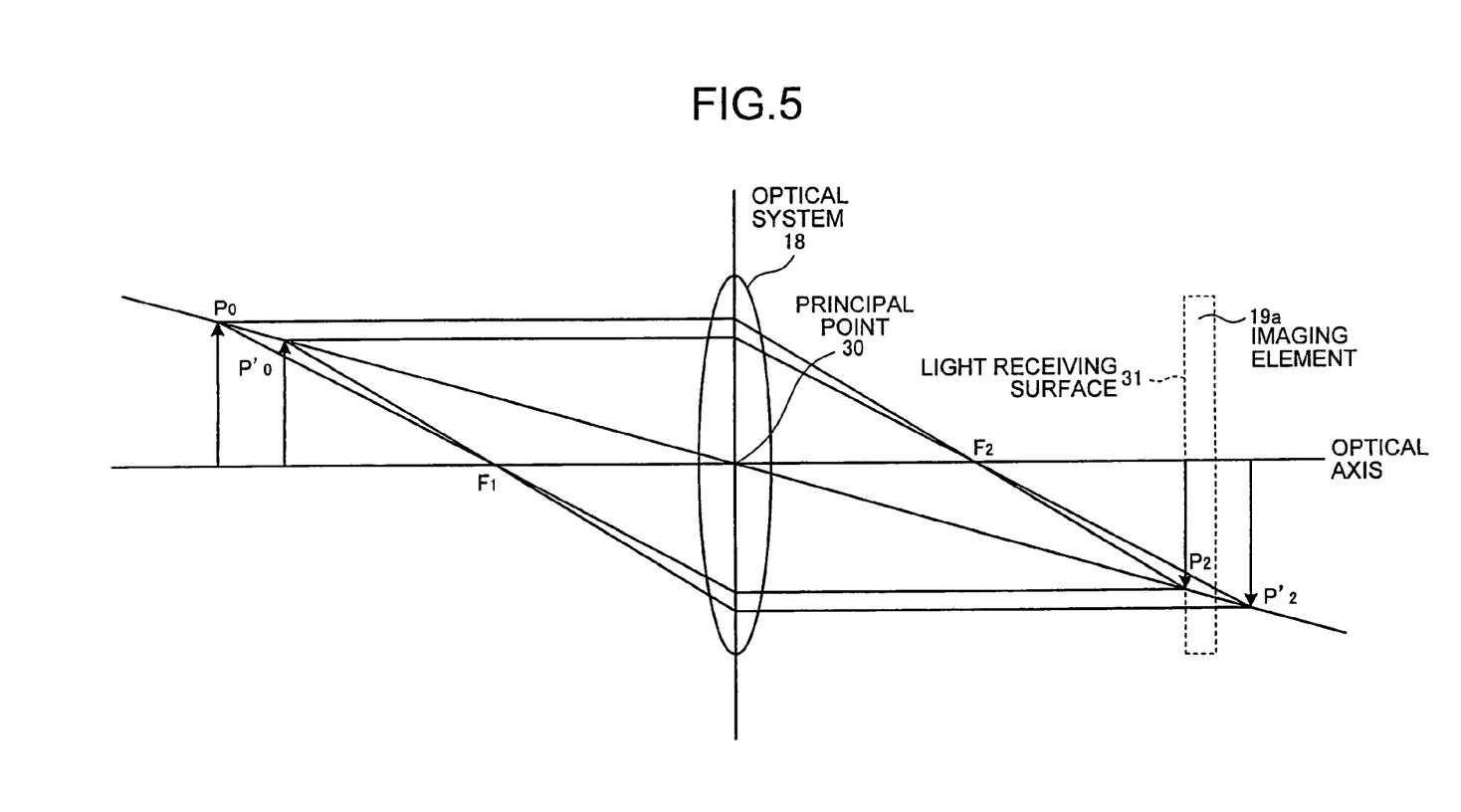
FIG. 5 is a schematic diagram illustrating an advantage of the capsule endoscope.

FIG. 5 is a schematic diagram illustrating a fundamental rule on how the image of the traction member 29 comes to appear in the intra-subject image captured by the imaging unit 19. In FIG. 5, off-axis object points $P_0$ and $P_0'$ are assumed to be present in a paraxial optical area. As shown in FIG. 5, when the off-axis object points $P_0$ and $P_0'$ are on the same straight line passing through the principal point 30 of the optical system 18, image points $P_2$ and $P_2'$ formed according to the function of the optical system 18 are on the same straight line.

Specifically, a partial component of the light emitted from the off-axis object point $P_0$ advances in the direction (horizontal direction in FIG. 5) of the optical axis of the optical system 18 and is refracted when passing through the optical system 18 to pass through a second focusing point $F_2$. On the other hand, a remaining component of the light emitted from the off-axis object point $P_0$ passes through a first focusing point $F_1$ to come into the optical system 18. After coming out from the optical system 18, the remaining component advances in a direction parallel to the direction of the optical axis due to refraction at the optical system 18. Further, a still remaining component of the light emitted from the off-axis object point $P_0$ advances straight toward the principal point 30 of the optical system 18, passes through the optical system 18 and advances without change in direction. As a result, the light emitted from the off-axis object point $P_0$ converges at a point $P_2$ after passing through the optical system 18, and the point $P_2$ becomes an image point. The same applies to the off-axis object point $P_0'$. Each component of light emitted from the off-axis object point $P_0'$ converges at a point $P_2'$ again after passing through the optical system 18, and the point $P_2'$ becomes an image point. Therefore, as is obvious from FIG. 5, the image points $P_2$ and $P_2'$ are formed on the same straight line as a straight line passing through the off-axis object points $P_0$ and $P_0'$ and the principal point 30.

The example shown in FIG. 5 relates to the off-axis object points and not to on-axis object points, i.e., points on the optical axis. However, when plural on-axis object points are on the optical axis, an image point corresponding to the plural on-axis object point on the same straight line (optical axis) passing through the principal point 30 is formed on the same straight line (optical axis), and therefore has the similar relation as the relation between the off-axis object points and the image shown in FIG. 5. Therefore, following description on the off-axis object points should be regarded to be similarly applied to the on-axis object points.

As shown in FIG. 5, when the imaging element 19a is arranged so that a light receiving surface 31 is arranged at a position where the image point $P_2$ is formed, the positions of the off-axis object points $P_0$ and $P_0'$ on the image data obtained by the imaging element 19a will be as follows. As described above, the image points $P_2$ and $P_2'$ of the off-axis object points $P_0$ and $P_0'$ are formed on the same straight line passing through the principal point. Since the straight line passes through the light receiving surface 31 at one point, the off-axis object points $P_0$ and $P_0'$ form an image at the same position on the light receiving surface 31. Due to difference in the distance from the optical system 18, an image of the off-axis object point $P_0'$ is slightly out of focus. Therefore, two images do not perfectly overlap with each other, and there is a slight misalignment in outer circumferences of the images. However, the misalignment of the outer circumferences caused by defocusing is trivial and centers of the images substantially coincide with each other. Therefore, plural images can be regarded to substantially completely overlap with each other.

Thus, when plural off-axis object points are present on the same straight line passing through the principal point 30 of the optical system 18, images corresponding to the plural off-axis object points overlap with each other on the light receiving surface 31 of the imaging element 19a. In the embodiment, such a fundamental rule is utilized to configure the attachment member 28 and the traction member 29 so as to reduce a degree of appearance of the traction member 29 in the intra-subject image.

In the embodiment, each portion of the attachment member 28 and the traction member 29 is regarded as a collection of the off-axis object points $P_0$ and $P_0'$ in FIG. 5, and the attachment member 28 and the traction member 29 are arranged so that the collection of the off-axis object points are present in the same direction relative to the principal point 30. Specifically, a direction of a position where the attachment member 28 is arranged from the principal point 30 is regarded as a reference direction, and the attachment member 28 and the traction member 29 are arranged so that the longitudinal direction of the attachment member 28 and the direction of extension of the traction member 29 coincide with the reference direction. With such a structure, images of the respective portions of the traction member 29 and the attachment member 28 overlap with each other in the intra-subject image focused by the optical system 18 and captured by the imaging unit 19, as described with reference to FIG. 5.

Figure 6:
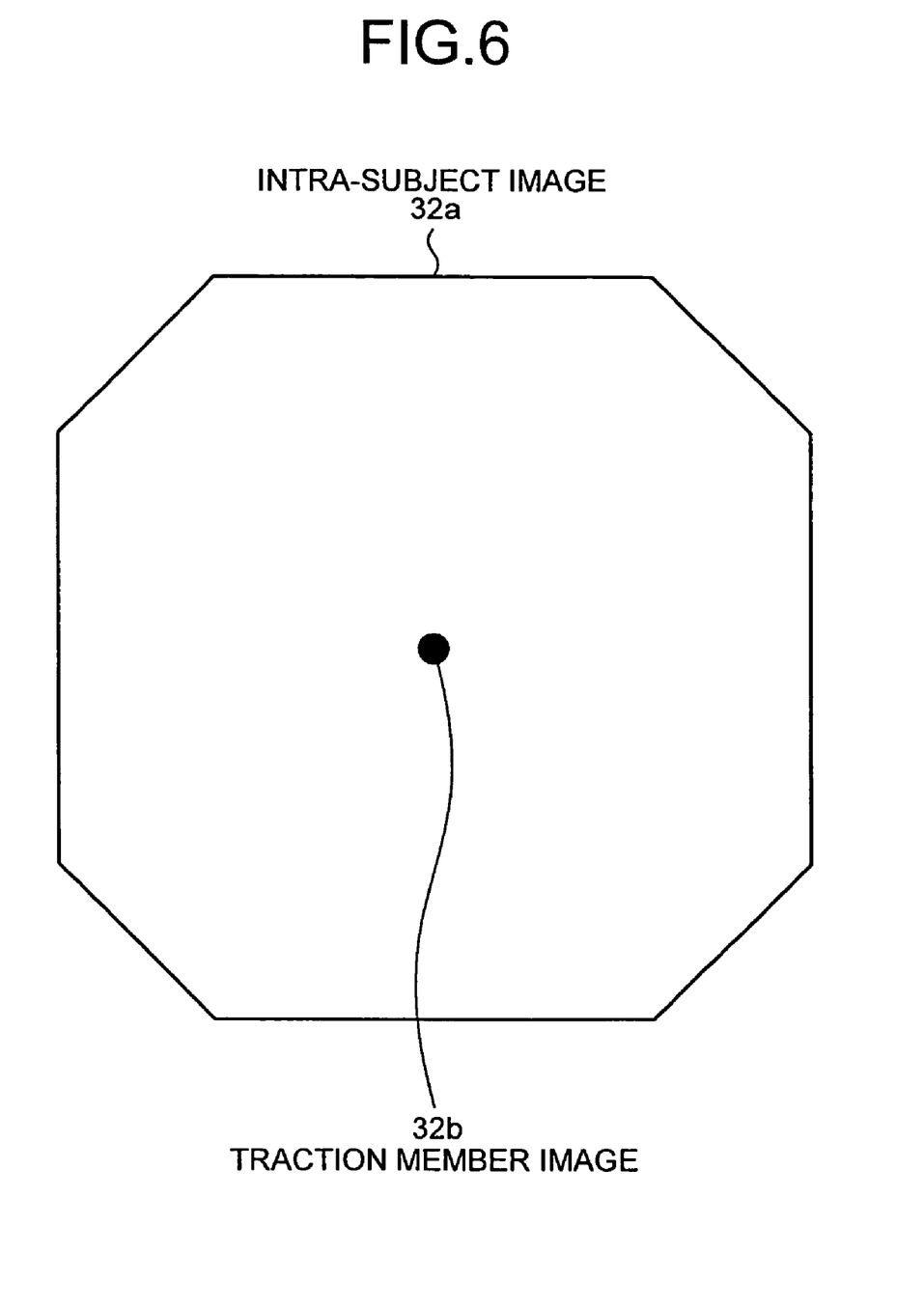
FIG. 6 is a schematic diagram of an intra-subject image captured by an imaging unit provided in the capsule endoscope.

FIG. 6 is a schematic diagram of a content of an intra-subject image 32a captured by the imaging unit 19. As shown in FIG. 6, in the intra-subject image 32a, a traction member image 32b (and attachment unit image) is represented substantially by one point, and therefore the image is prevented from extending linearly over the entire image as shown in FIG. 10. Therefore, the body-insertable apparatus system of the embodiment can suppress the appearance of the traction member 29 and the attachment member 28 in the intra-subject image captured by the imaging unit 19. Thus, the imaging unit 19 can capture a high-quality intra-subject image, and the appearance of the traction member 29 or the like would not hamper the diagnosis and observation by the doctor or the like.

Further, since the inside of the subject 1 is extremely dark, the capsule endoscope 2 includes the illuminating unit 24, and the illuminating light emitted from the illuminating unit 24 is reflected and comes into the optical system 18. In the capsule endoscope 2 in which the traction member 29 and the attachment member 28 are arrange din the direction of emission of the illuminating light, the traction member 29 or the like may obstruct the propagation of the illuminating light and the reflected light. However, since the traction member 29 and the attachment member 28 are formed as described above in the embodiment, it is possible to suppress the obstruction of the propagation of the illuminating light and the reflected light by the traction member 29 or the like, and it is possible to make the light of sufficient intensity for imaging to come into the optical system 18. Further, since the traction member 29 has the above described structure, the diffused reflection of the illuminating light and the reflected light by the traction member 29 can be suppressed, and the flare or the like on the intra-subject image can also be suppressed.

Further, the capsule endoscope 2 of the embodiment has the structure in which the optical system 18 is arranged so that the direction of the optical axis of the optical system 18 coincides with the longitudinal direction of the outer casing member 17, and the traction member 29 and the attachment member 28 are arranged on the optical axis. As a result, the direction of extension of the traction member 29 coincides with the longitudinal direction of the outer casing member 17 as shown in FIG. 3. Since the direction of extension of the traction member 29 coincides with the longitudinal direction of the outer casing member 17, the capsule endoscope 2 is prevented from vibrating in a direction perpendicular to the direction of traction while the capsule endoscope 2 is pulled with the use of the traction member 29, whereby damages to the subject 1 can be prevented and the capsule endoscope 2 can be pulled smoothly.

First Modification

Figure 7:
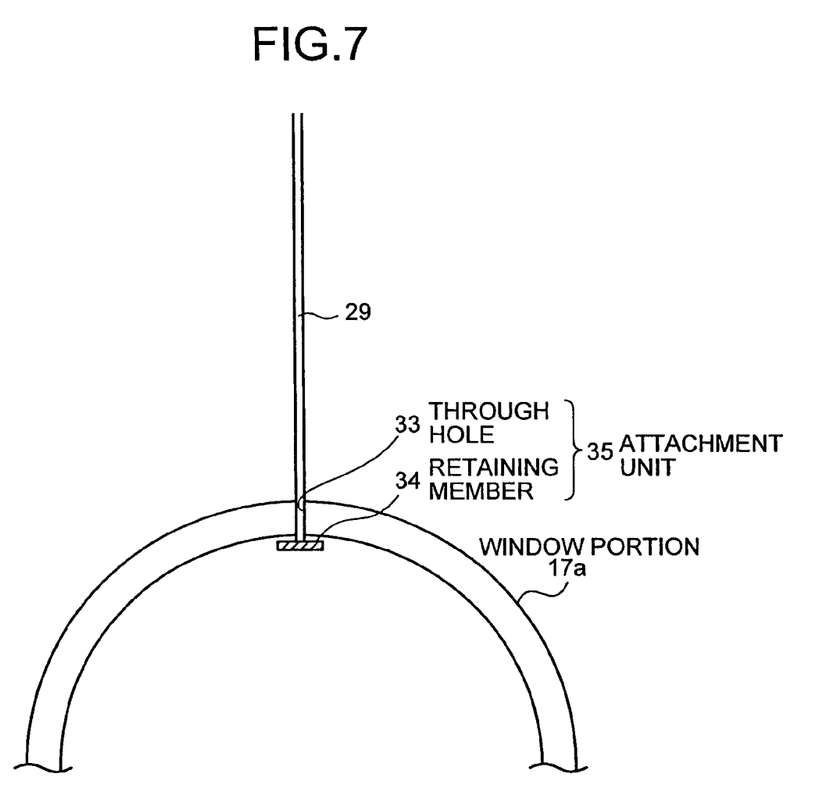
FIG. 7 is a schematic diagram of a structure of an attachment unit provided in a capsule endoscope according to a modification.

A first modification of the body-insertable apparatus system according to the embodiment will be described. FIG. 7 is a schematic diagram of a structure of an attachment unit 35 of a capsule endoscope according to the first modification. As shown in FIG. 7, the attachment unit 35 is formed on the window portion 17a and includes a through hole 33 which let a proximal end of the traction member 29 pass through, and a retaining member 34 which serves to retain the proximal end of the traction member 29 penetrating the through hole 33. Even when the capsule endoscope has the above described structure, the same advantages as those of the above mentioned embodiment can be obtained.

Here, it is preferable that the attachment unit 35 be formed so that the longitudinal direction of the attachment unit 35 coincides with the direction from the principal point 30 to the position of the attachment unit 35. Specifically in the first modification, it is preferable that the attachment unit 35 is formed so that a penetrating direction of the through hole 33 coincides with the direction from the principal point 30 to the position of the attachment unit 35.

Second Modification

Figure 8:
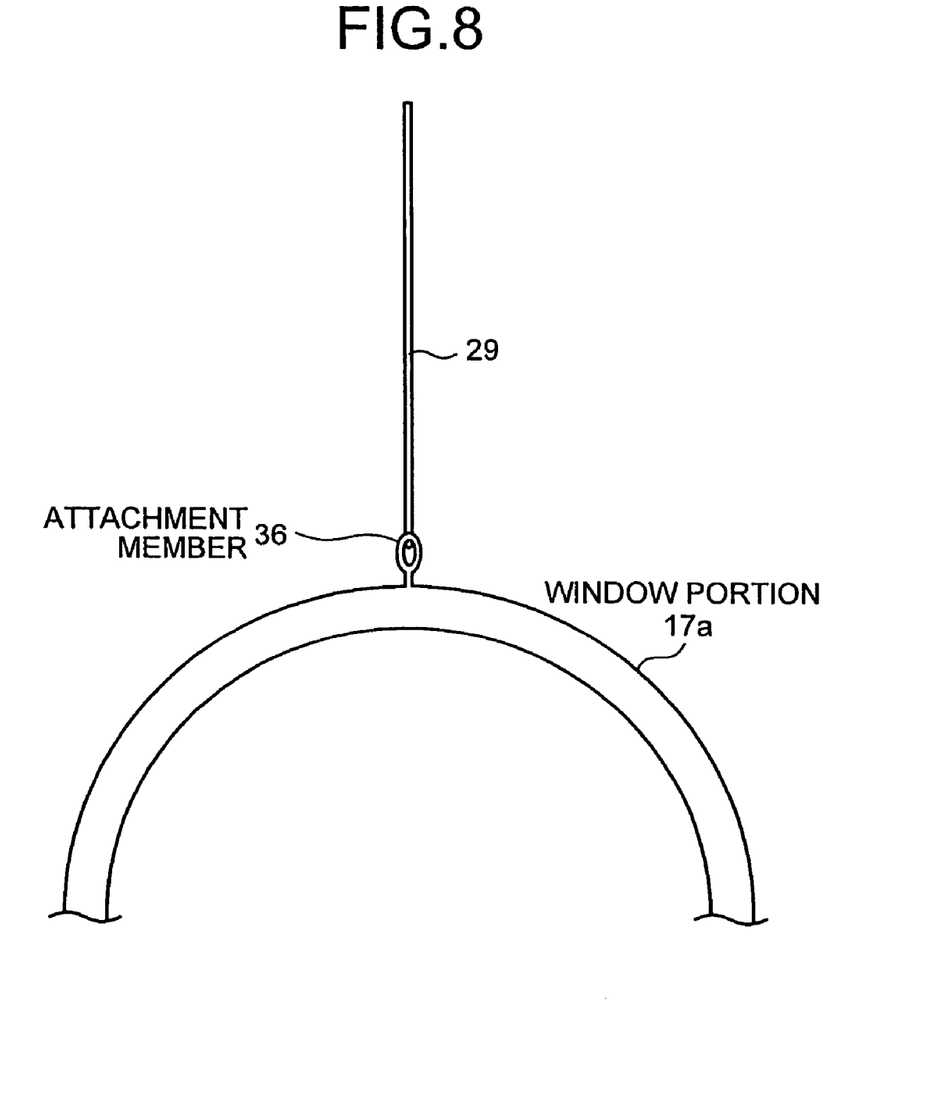
FIG. 8 is a schematic diagram of a structure of an attachment unit provided in a capsule endoscope according to another modification.

A second modification of the body-insertable apparatus system according to the embodiment will be described. FIG. 8 is a schematic diagram of a structure of an attachment member 36 of a capsule endoscope according to the second modification. As shown in FIG. 8, even when the attachment member 36 is formed integrally with the window portion 17a, the same advantages as those of the above mentioned embodiments can be obtained.

INDUSTRIAL APPLICABILITY

As can be seen from the foregoing, the body-insertable apparatus and the body-insertable apparatus system according to the present invention are useful as a body-insertable apparatus which is introduced into the subject and captures intra-subject images, and as a body-insertable apparatus system including the body-insertable apparatus, and particularly suitable for a body-insertable apparatus system including a capsule endoscope as the body-insertable apparatus.

The invention claimed is:

1. A body insertable apparatus which is introduced inside a subject and travels through the inside of the subject, comprising:
    an optical system which focuses light introduced from outside onto a predetermined surface;
    an outer casing member which houses the optical system and includes a window portion to introduce light from outside into the optical system;
    an attachment member which is formed at a predetermined portion of the window portion; and
    a traction member whose one end is secured by the attachment member and which extends by a predetermined distance towards an outside of the window portion in a direction from a principal point of the optical system toward the predetermined portion.

2. The body insertable apparatus according to claim 1 wherein
    the attachment member is formed on a portion on an extension of an optical axis of the optical system in the window portion, and
    the traction member is arranged so that the traction member extends by the predetermined distance on the extension of the optical axis of the optical system.

3. The body insertable apparatus according to claim 1, wherein the attachment member is formed so that a longitudinal direction of the attachment member coincides with the direction from the principal point of the optical system toward the predetermined portion.

4. The body insertable apparatus according to claim 2, wherein the attachment member is formed so that a longitudinal direction of the attachment member coincides with the direction from the principal point of the optical system toward the predetermined portion.

5. The body insertable apparatus according to claim 1, wherein the optical system is arranged so that a direction of an optical axis coincides with a central axis in a longitudinal direction of the outer casing member.

6. The body insertable apparatus according to claim 2, wherein the optical system is arranged so that a direction of an optical axis coincides with a central axis in a longitudinal direction of the outer casing member.

7. The body insertable apparatus according to claim 3, wherein the optical system is arranged so that a direction of an optical axis coincides with a central axis in a longitudinal direction of the outer casing member.

8. The body insertable apparatus according to claim 4, wherein the optical system is arranged so that a direction of an optical axis coincides with a central axis in a longitudinal direction of the outer casing member.

9. The body insertable apparatus according to claim 1, further comprising:
    an imaging unit which generates image data based on light focused by the optical system; and
    a transmitting unit which transmits a radio signal containing the image data generated.

10. The body insertable apparatus according to claim 2, further comprising:
    an imaging unit which generates image data based on light focused by the optical system; and a transmitting unit which transmits a radio signal containing the image data generated.

11. The body insertable apparatus according to claim 3, further comprising
an imaging unit which generates image data based on light focused by the optical system; and
a transmitting unit which transmits a radio signal containing the image data generated.

12. The body insertable apparatus according to claim 4, further comprising:
an imaging unit which generates image data based on light focused by the optical system; and
a transmitting unit which transmits a radio signal containing the image data generated.

13. The body insertable apparatus according to claim 5, further comprising:
an imaging unit which generates image data based on light focused by the optical system; and
a transmitting unit which transmits a radio signal containing the image data generated.

14. The body insertable apparatus according to claim 6, further comprising:
an imaging unit which generates image data based on light focused by the optical system; and
a transmitting unit which transmits a radio signal containing the image data generated.

15. The body insertable apparatus according to claim 7, further comprising:
an imaging unit which generates image data based on light focused by the optical system; and
a transmitting unit which transmits a radio signal containing the image data generated.

16. The body insertable apparatus according to claim 8, further comprising:
an imaging unit which generates image data based on light focused by the optical system; and
a transmitting unit which transmits a radio signal containing the image data generated.

17. A body-insertable apparatus system, comprising:
a body insertable apparatus which is introduced inside a subject, captures an intra-subject image, and transmits a radio signal containing the intra-subject image captured; and
a receiving device which receives the radio signal transmitted from the body insertable apparatus, wherein
the body insertable apparatus includes
an optical system which focuses light introduced from outside onto a predetermined surface,
an outer casing member which houses the optical system and includes a window portion to introduce light from outside to a field of view defined by the optical system, and
a traction member whose one end is secured by an attachment member formed at a predetermined portion of the window portion and which extends by a predetermined distance towards an outside of the window portion in a direction from a principal point of the optical system toward the predetermined portion, and
the receiving device includes
a receiving circuit which performs a predetermined receiving process on the radio signal received by a receiving antenna, and
a signal processing unit which extracts image information from a signal subjected to the receiving process by the receiving circuit.

18. The body-insertable apparatus according to claim 1, wherein the traction member is a string-like member.

19. The body-insertable apparatus according to claim 1, wherein after the body-insertable apparatus is introduced inside the subject, a travel speed of the body-insertable apparatus inside the subject can be controlled by manipulation of the traction member.

20. The body-insertable apparatus according to claim 1, wherein the traction member is treated to prevent reflection.

21. The body-insertable apparatus according to claim 1, wherein the traction member is formed from a biocompatible material or is absorbed by the subject over time.

22. The body-insertable apparatus according to claim 1, wherein an end of the extension of the traction member is located further than a focusing point of the optical system from the attachment member.

* * * * *